United States Patent
Bleicher et al.

(10) Patent No.: US 9,383,339 B2
(45) Date of Patent: Jul. 5, 2016

(54) METHOD FOR INSPECTING A COMPONENT ON THE BASIS OF BARKHAUSEN NOISES

(71) Applicant: ZF Friedrichshafen AG, Friedrichshafen (DE)

(72) Inventors: Oliver Bleicher, Vancouver (CA); Herman Yakaria, Langenargen (DE); Yiwen Xu, Friedrichshafen (DE)

(73) Assignee: ZF Friedrichshafen AG, Friedrichshafen (DE)

( * ) Notice: Subject to any disclaimer, the term of this patent is extended or adjusted under 35 U.S.C. 154(b) by 66 days.

(21) Appl. No.: 14/385,800

(22) PCT Filed: Mar. 4, 2013

(86) PCT No.: PCT/EP2013/054230
§ 371 (c)(1),
(2) Date: Sep. 17, 2014

(87) PCT Pub. No.: WO2013/149776
PCT Pub. Date: Oct. 10, 2013

(65) Prior Publication Data
US 2015/0054501 A1    Feb. 26, 2015

(30) Foreign Application Priority Data
Apr. 5, 2012 (DE) .................. 10 2012 205 677

(51) Int. Cl.
*G01N 27/72* (2006.01)
*G01N 27/82* (2006.01)
*G01R 33/06* (2006.01)

(52) U.S. Cl.
CPC ............. *G01N 27/82* (2013.01); *G01R 33/06* (2013.01); *G01N 27/725* (2013.01)

(58) Field of Classification Search
CPC ....... G01N 27/725; G01N 27/82; G01R 33/06
USPC .................................................. 324/228–243
See application file for complete search history.

(56) References Cited

U.S. PATENT DOCUMENTS

| 3,783,370 A | 1/1974 | Birdwell et al. |
| 4,881,030 A | 11/1989 | Stuecker et al. |
| 5,619,135 A | 4/1997 | Kohn et al. |
| 5,992,241 A * | 11/1999 | Posgay ................ G01N 27/725 324/209 |

FOREIGN PATENT DOCUMENTS

| DE | 43 33 830 A1 | 4/1995 |
| DE | 196 01 027 A1 | 7/1997 |

(Continued)

OTHER PUBLICATIONS

T. Garstka, "The Influence of Product Thickness of the Measurements by Barkhausen Noise Method", Journal of Achievements in Materials and Manufacturing Engineering, Mar. 2008, vol. 27, issue 1, International OCSCO World Press, 4 pages.

(Continued)

*Primary Examiner* — Jay Patidar
(74) *Attorney, Agent, or Firm* — Davis & Bujold PLLC; Michael J. Bujold (57) ABSTRACT

A method of inspecting a component (1) on the basis of Barkhausen noises in which a plurality of Barkhausen noise signals are processed, which have been or are determined at measurement positions (PS1, PS2, . . . , PS9) along the surface of the component (1) by a measuring device. According to the method, a computer forms a measurement matrix (M) from the Barkhausen noise signals, which matrix contains the Barkhausen noise signals detected as entries. A variety of characteristics are specified, each of which represents at least one cause of a manufacturing defect(s) of the component (1), each characteristic is associated with a processing procedure of the measurement matrix (M). The procedure is specific for the characteristic concerned. Finally, for each characteristic the measurement matrix (M) undergoes the associated processing procedure in which the intensity of the characteristic concerned is determined.

12 Claims, 5 Drawing Sheets

(56) References Cited

FOREIGN PATENT DOCUMENTS

| | | |
|---|---|---|
| DE | 10 2007 001 464 A1 | 7/2008 |
| EP | 0 100 009 A1 | 2/1984 |
| EP | 0 125 064 A2 | 11/1984 |
| EP | 0 287 873 A2 | 10/1988 |
| WO | 96/10744 A1 | 4/1996 |
| WO | 2008/080395 A2 | 7/2008 |

OTHER PUBLICATIONS

Suvi Santa-Aho et al, "Development of Barkhausen Noise Calibration Blocks for Reliable Grinding Burn Detection", Journal of Materials Processing Technology, Oct. 4, 2011, vol. 212, No. 2, pp. 408-416, Elsevier, Netherlands, 9 pages.
German Search Report Corresponding to 10 2012 205 676.9 mailed Jan. 2, 2013, 6 pages.
German Search Report Corresponding to 10 2012 205 677.7 mailed Jan. 2, 2013, 6 pages.
International Search Report Corresponding to PCT/EP2013/054229 mailed May 21, 2013, 7 pages.
International Search Report Corresponding to PCT/EP2013/054230 mailed May 27, 2013, 4 pages.
Written Opinion Corresponding to PCT/EP2013/054230 mailed May 27, 2013, 7 pages.

\* cited by examiner

METHOD FOR INSPECTING A COMPONENT ON THE BASIS OF BARKHAUSEN NOISES

This application is a National Stage completion of PCT/EP2013/054230 filed Mar. 4, 2013, which claims priority from German patent application serial no. 10 2012 205 677.7 filed Apr. 5, 2012.

FIELD OF THE INVENTION

The invention concerns a method and a device for inspecting a component on the basis of Barkhausen noises.

BACKGROUND OF THE INVENTION

In the industrial production of components, during surface machining damage may occur. Particularly in the mass production of components it is therefore necessary by means of a suitable inspection method to recognize such damage so that the damaged components can be separated out and the production process modified so as to avoid it.

A frequently occurring form of surface damage is the so-termed grinding burn, which for example can take place during tooth grinding to produce the final contour of toothed components. For the recognition of surface damage or grinding burn, from the prior art chemical etching methods are known. During so-termed Nital etching the component to be inspected is treated with various acids and electrolytes such that after the treatment, surface damage and particularly grinding burn can be recognized by virtue of color changes on the component. Nital etching is on the one hand not environmentally friendly, and on the other hand it incurs very high costs for the maintenance and disposal of the acids and electrolytes used. Furthermore, it is a subjective inspection method in which the surface damage is assessed by human experts by virtue of the discoloration. Thus, Nital etching is not suitable for inspecting the surface of components in the context of mass production.

From the prior art the so-termed Barkhausen Noise Analysis is also known, with which the surface of ferromagnetic materials can be inspected by means of appropriate sensors. In the documents EP 0 100 009 A1 and DE 43 33 830 A1 methods for surface analysis taking account of Barkhausen noises are described. Barkhausen Noise Analysis is based on the so-termed Barkhausen jumps, which are produced by the reversal of magnetization in ferromagnetic materials in a magnetic field of slowly increasing strength. Ferromagnetic materials consist of small magnetic regions (called domains) with a uniform magnetization direction. The domains are separated from one another by Bloch walls, within which the magnetization direction changes through the width of the walls. A movement of the Bloch walls can be brought about by an external magnetic field. If at the same time a coil is positioned close to the ferromagnetic component, the magnetization produces an electric pulse in the coil. Addition of the impulses produces a noise-like signal, also known as Barkhausen noise or a Barkhausen noise signal. The Barkhausen noise signal depends on the surface condition and in particular on the surface hardness. By means of the Barkhausen noise signal grinding burn can be detected, since grinding burn reduces the surface hardness.

Even though by way of Barkhausen noise analysis surface damage can be recognized, the present analysis methods do not provide any conclusions about the causes, during the production process of the component, that have resulted in the surface damage. Accordingly, it is desirable to extend Barkhausen noise analysis in such manner that the causes of surface damage are recognized.

SUMMARY OF THE INVENTION

The purpose of the present invention is therefore to provide a method and device for inspecting a component on the basis of Barkhausen noises, which determine the causes of component damage.

This objective is achieved by the method and device described below.

In the method according to the invention a large number of Barkhausen noise signals are processed, which signals have been or are detected by means of a suitable measuring device at measurement positions along the surface of the component for the purpose of Barkhausen noise analysis. The step of detecting the Barkhausen noise signals can therefore be part of the method according to the invention. However, it is also possible for the method according to the invention to begin from Barkhausen noise signals already detected earlier, which are for example read out from an appropriate memory. The method according to the invention is carried out with digital processing support by a computer unit. During the process, a measurement matrix is first formed from the Barkhausen noise signals, the matrix contains as entry values the Barkhausen noise signals detected. Furthermore a plurality of characteristics are specified, which in each case represent at least one cause of manufacturing defects of the component, such as causes of grinding burn or other processing defects during production. The plurality of characteristics can for example be stored in advance in a memory. Each characteristic is associated with a processing procedure of the measurement matrix. The procedure is specific to the characteristic concerned, so that with the corresponding processing procedure conclusions can be drawn about causes of manufacturing defects. Finally, for each characteristic the measurement matrix undergoes the associated procedure whereby an intensity of the characteristic concerned is determined.

The method according to the invention is based on the recognition that characteristics can appropriately be linked with special processing steps for the Barkhausen noise signals that are applicable for the characteristic in each case, in order to determine from this causes of component damage. In the method according to the invention, in particular Barkhausen noise signals from components are processed, for which it is already known that surface damage or grinding burn is present. Example embodiments of processing steps that correspond to the specification for each characteristic are described in more detail later.

In a particularly preferred embodiment, the method for inspecting a gearwheel is used, wherein the measurement positions at which the Barkhausen noise signals are or have been determined are three-dimensional measurement positions that include the dimensions of gearwheel circumference, tooth profile and gearwheel width. In this case the gearwheel circumference covers tooth flanks and tooth gaps along the gearwheel circumference, the tooth profile concerns measurement lines for a tooth gap or a tooth flank, and the tooth width specifies width positions in the direction of the width of the gearwheel.

In another, particularly preferred embodiment the respective characteristics define one or more of the following causes: concentricity errors, one-sided grinding, unprocessed areas, dimensional fluctuations, hardening distortions, deviant component surface hardness values, tool wear and the like. If needs be, measurement errors such as lack of contact between the measuring body and the component, or a defective measuring sensor, can be taken into account as characteristics.

In a preferred embodiment of the method according to the invention, the processing procedure associated with each respective characteristic is designed in such manner that a specific correction matrix with correction values specific for the characteristic concerned is specified for each entry in the measurement matrix and the sum of the measurement matrix entries multiplied by the correction values is formed, this sum then representing an absolute intensity of the characteristic concerned. Depending on the design of the invention the correction values can be determined in different ways. In a preferred variant the correction values used are one and zero.

In a particularly preferred embodiment of the invention, in which a gearwheel is inspected, the correction values for the characteristic of concentricity error, for all the Barkhausen noise signals with measurement positions within a predetermined circumferential region, are set to one and otherwise to zero. This takes into account that concentricity errors in a predetermined circumferential region result in grinding burn and therefore in elevated Barkhausen noise signals, which are particularly strongly weighted. For the characteristic of one-sided grinding the correction values can be set such that they alternate between zero and one from one tooth flank to the next, but are the same within a tooth flank. In this way one-sided grinding can be detected, in which grinding burn occurs only on one tooth flank. Likewise, one-sided grinding along the width of the gearwheel can be recognized if correction values along an edge area of the width of the gearwheel are set as one and otherwise zero.

In another embodiment of the method according to the invention, the processing procedure associated with each respective characteristic comprises a modification step in accordance with which a modified measurement matrix is determined by averaging the Barkhausen noise signals from a number of measurement positions along the surface of the component, the number of measurement positions being specific for the characteristic concerned. In a preferred variant for the characteristic of concentricity error, the measurement positions whose Barkhausen noise signals are averaged are exclusively measurement positions that relate to the same tooth flank or tooth gap, so that no averaging takes place over the circumference of the gearwheel. For the characteristic of one-sided grinding the measurement positions whose Barkhausen noise signals are averaged are preferably only ones that relate to the same tooth flank or the same width position of the gearwheel width. For averaged measurement positions that relate to the same tooth flank, different grinding of the right-hand and left-hand tooth flanks can be considered as a characteristic. For averaged measurement positions relating to the same width position one-sided grinding along the gearwheel width can be considered as a characteristic. In a preferred embodiment, for the characteristic of concentricity error the measurement positions whose Barkhausen noise signals are averaged relate to various measurement lines at the same width position of the gearwheel and also concern the same tooth flank.

In a further particularly preferred embodiment, besides the above-described modification step the processing procedure associated with each respective characteristic comprises a processing step in accordance with which the entries in the modified measurement matrix are discretized and a concurrence matrix for the frequency of value combinations of neighboring entries in the modified and discretized measurement matrix is determined, the concurrence matrix then being multiplied by a weighting matrix which assigns greater weight to large changes in the values of neighboring entries in the modified and discretized measurement matrix, wherein the determinant of the multiplication result is calculated. This determinant represents an absolute intensity for the respective characteristic concerned. This embodiment makes use of the knowledge that characteristics can be detected very effectively by virtue of marked fluctuations of the Barkhausen noise signals along the component. In a known way, these marked fluctuations are described by a co-occurrence matrix known from the field of image processing, which is also called the gray scale value matrix. Instead of being used for the gray scale values in images, that matrix is here used for corresponding values of Barkhausen noise signals.

In the above-described embodiments which determine an absolute intensity of the respective characteristic, from the absolute intensity it is preferable to determine a relative intensity since the absolute intensity of the characteristic concerned is part of the sum of the absolute intensities of all the characteristics.

Besides the above-mentioned method, the invention also concerns a device for the inspection of a component on the basis of Barkhausen noises, using a large number of Barkhausen noise signals which have been or are determined by means of a measuring device at measurement positions along the surface of the component. The device according to the invention comprises a computer unit designed such that during its operation a measurement matrix is formed from the Barkhausen noise signals, which matrix contains as entries the Barkhausen noise signals detected. Furthermore, by means of the computer unit a plurality of characteristics are specified, each of which represents at least one cause of manufacturing defects in the component, and wherein each characteristic is associated with a processing procedure of the measurement matrix, the procedure being specific for the respective characteristic concerned. Finally, for each characteristic the measurement matrix undergoes the associated processing procedure, whereby an intensity of the characteristic is determined.

The device according to the invention is preferably designed such that one or more variants of the above-described, preferred embodiments of the method according to the invention can be carried out with the device. The device can if necessary be part of the measuring device by means of which the Barkhausen noise signals are detected. Likewise, however, the device can be a separate evaluating unit for Barkhausen noise signals.

BRIEF DESCRIPTION OF THE DRAWINGS

Example embodiments of the invention are described in detail below with reference to the attached figures, which show.

DETAILED DESCRIPTION OF THE PREFERRED EMBODIMENTS

Below, the method according to the invention is explained on the basis of the surface inspection of components in the form of gearwheels. Nonetheless, the invention can also be used for components of any other type. In the present case, during the manufacture of the gearwheels their final contour is produced by tooth-grinding. During this grinding process the excess material is worn away by grinding grains. This can cause the local temperatures at the contact zone to change so markedly that thermal structural changes take place. These thermal structural changes are often known as grinding burn. It is one objective of the embodiment of the invention described here, by means of an appropriately calibrated measuring device, to recognize such components as have surfaces damaged by grinding burn. Grinding burn is produced, inter alia, if the component-specific annealing temperature is exceeded and occurs in the form of tempering damage as a result of which the hardness at the points affected in the component decreases. If the temperature is increased drastically followed by cooling due to the coolant medium a harder surface is produced. That form of grinding burn is also referred to as re-hardening.

In the embodiment described here Barkhausen noise signals from gearwheels are first detected by means of a measuring device. The measuring device is calibrated appropriately so that damaged components with grinding burn are recognized from the measured values. The measured values determined from damaged components then undergo an evaluation in order to identify the most probable causes for the grinding burn or processing defects during the production of the component. As already explained earlier, Barkhausen noises are measured by applying an external magnetic field at corresponding points of the surface of a component just inspected. By means of a coil of conductive wire the magnetization produced gives rise to an electrical pulse in the coil, which depends on the surface hardness. By addition of the electric pulses $x_i$ a noise-like signal is obtained. Then, as a rule, the effective value of the Barkhausen signal is used as a measurement value, which is given by the following equation:

$$mp = \sqrt{\frac{1}{n}\sum_{i=0}^{n-1} x_i^2}. \tag{1}$$

The abbreviation mp, known per se, in this case represents the magnetic parameter.

Figure 1:
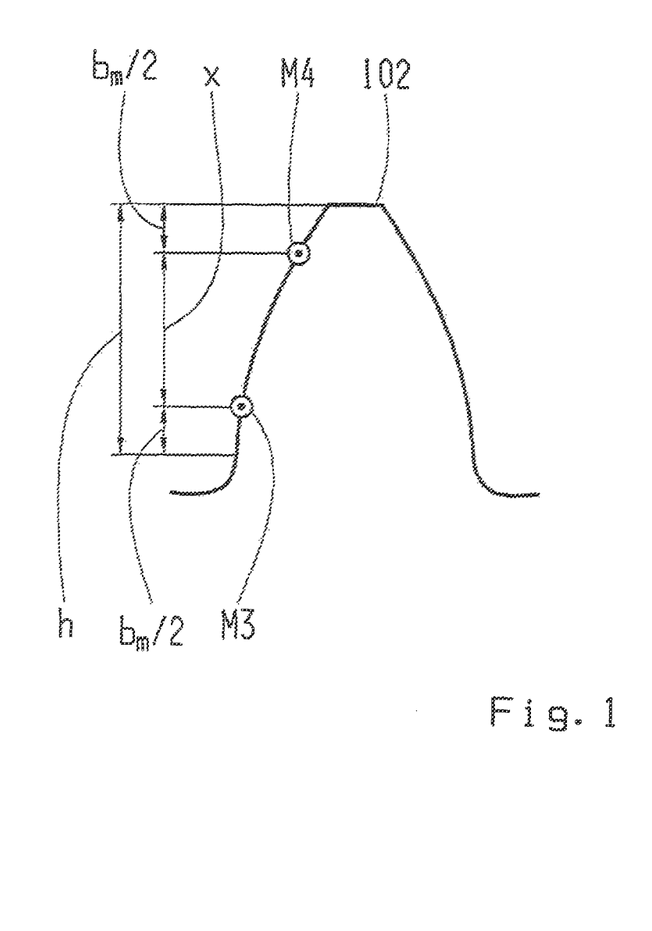
FIGS. 1 and 1A: A schematic representation of a measurement method based on Barkhausen noises for a gearwheel.
Figure 1A:
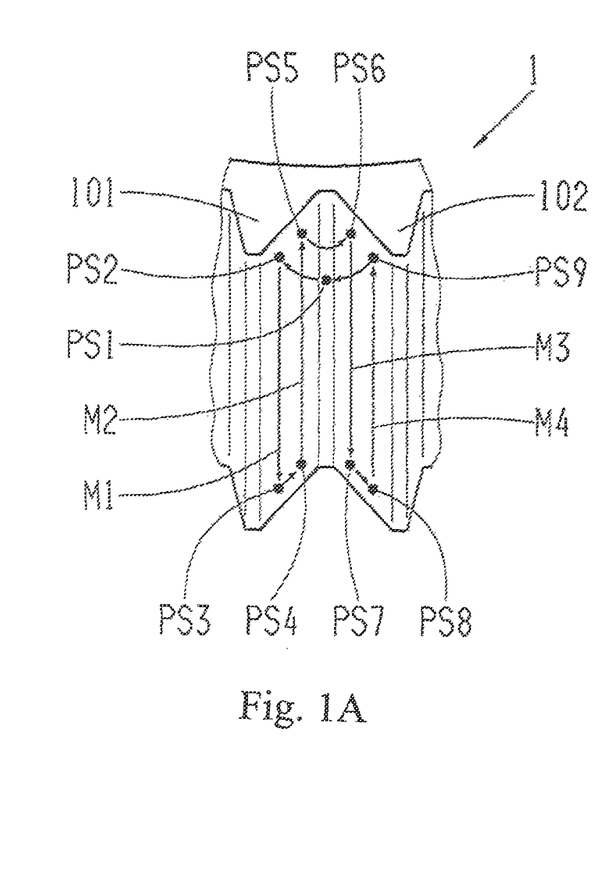

FIG. 1 makes clear a measurement sequence for determining the Barkhausen noise from a gearwheel. FIG. 1A shows a perspective view of a tooth gap of the gearwheel. This tooth gap is between the two teeth 101 and 102, which are only shown in part. To measure the Barkhausen noise signal, an appropriate sensor head of the measuring device is moved along measurement lines M1 to M4 so that as it moves continuously, the Barkhausen noise signal is measured. FIG. 1A shows as an example, a measurement sequence in which the measuring head starts at point PS1, moves to the surface point PS2 on the tooth 101, and then along the measurement line M1 to point PS3. Thereafter, further measurements are made from point PS4 to point PS5 along the measurement line M2. By analogy, for the tooth 102 measurements are made first along the measurement line M3 from point PS6 to point PS7 and finally along the measurement line M4 from point PS8 to point PS9. FIG. 1 shows a sectioned view of the tooth 102. The measurement lines M3 and M4 are shown to be perpendicular to the plane of the drawing. The dimension h shows the tooth height that is useful for measurements, while $b_m/2$ are the corresponding distances of the measurement lines M3 and M4, respectively from the lower and upper ends of the useful tooth height. The distance between M3 and M4 is indexed x.

The signal intensities of the Barkhausen noises for well-prepared (i.e. dirt-free and oil-free) components are influenced by the internal stresses and the hardness of the component. For example, a reduction of the compression condition results in an increase of the Barkhausen noise amplitude. When the hardness changes, the contrary is observed, i.e. as the hardness increases the Barkhausen noise amplitude decreases. Thus, with an appropriately calibrated device the presence of grinding burn can be concluded from the Barkhausen noise signals obtained from a component. In the embodiment described here, the Barkhausen noise signals from a component are now evaluated further, in order to correlate the signals with causes of the grinding burn or processing defects during the production of the component.

Figure 2:
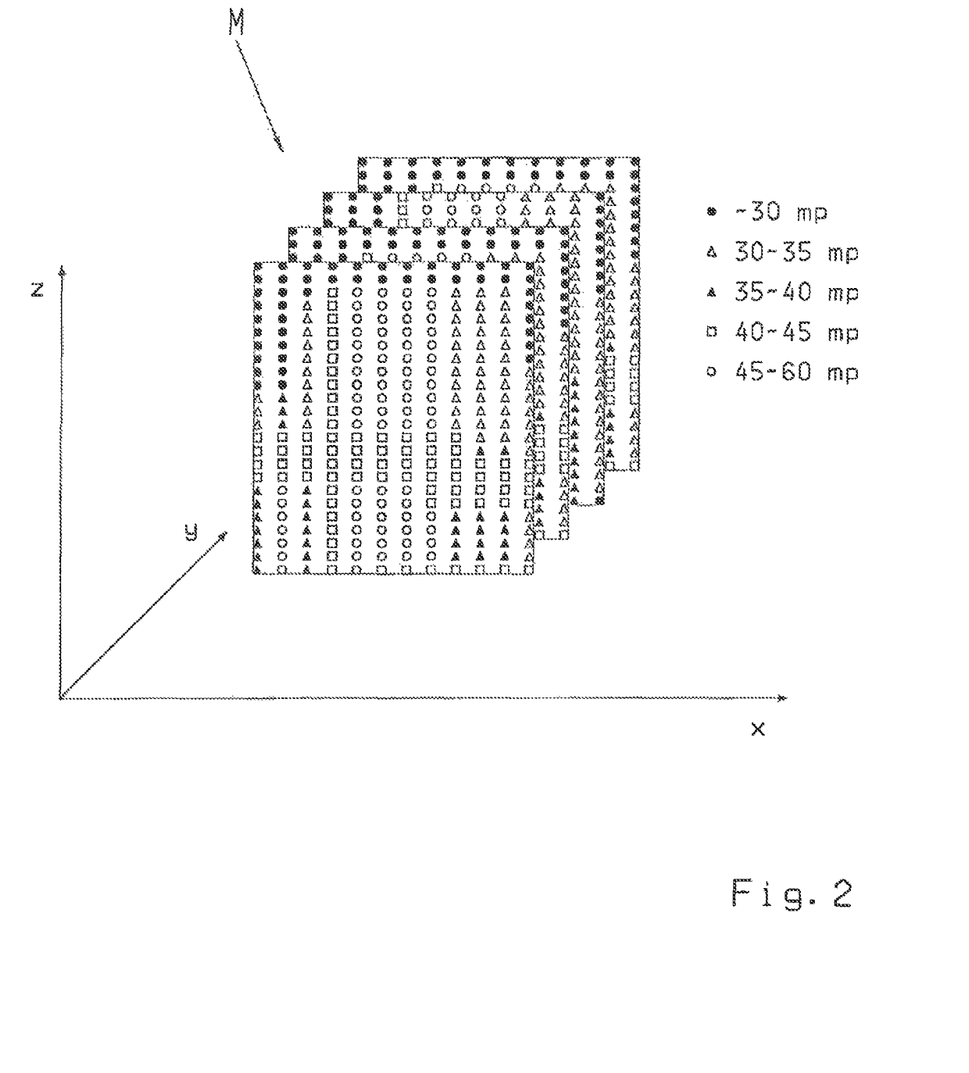
FIG. 2: A graphical representation of a measurement matrix of Barkhausen noise signals, which is processed in an embodiment of the method according to the invention.

The Barkhausen noise signals are evaluated by means of a computer unit which processes the measured values obtained from a gearwheel into the form of a measurement matrix. FIG. 2 shows a visual presentation of such a measurement matrix M in the form of a three-dimensional array of measurement points. In this case each measurement point represents a corresponding position along the surface of the component from which a Barkhausen noise signal has been determined. By virtue of the color or brightness of the individual measurement points, the intensity of the Barkhausen noise signal is coded. As can be seen from the legends on the right in FIG. 2, darker points represent higher Barkhausen noise signals and lighter points represent lower Barkhausen noise signals. Corresponding value ranges of the Barkhausen noise signals are coded by a color or brightness value in accordance with the legends. If necessary the Barkhausen noise signals can also be discretized on the basis of the value ranges shown by the legends, in that they are associated with corresponding discrete intensity values or classes. In the representation shown in FIG. 2, the x-axis represents the component circumference of the gearwheel, and the vertical columns arranged in alternation in the direction of the x-axis represent right-hand and left-hand tooth flanks of the gearwheel. In a different embodiment, the individual columns can also be associated with a corresponding tooth gap. The y-axis in FIG. 2 represents the tooth profile in the form of the corresponding measurement lines per tooth flank. Otherwise than in the representation in FIG. 1, for each tooth flank not two, but four measurement lines are considered. The z-axis of FIG. 2 represents corresponding positions along a respective measurement line, and thus width positions of the gearwheel.

The graphically represented measurement matrix in FIG. 2 can be described mathematically as follows:

$$M = \begin{bmatrix} x_1 & y_1 & z_1 & s_{1,1,1} \\ \ldots & \ldots & \ldots & \ldots \\ x_u & y_1 & z_1 & s_{u,1,1} \\ \ldots & \ldots & \ldots & \ldots \\ x_u & y_v & z_1 & s_{u,v,1} \\ \ldots & \ldots & \ldots & \ldots \\ x_u & y_v & z_w & s_{u,v,w} \end{bmatrix}. \tag{1}$$

in which $s_{u,v,w}$ is the signal intensity at the coordinates $[x_u, y_v, z_w]$.

For each of the measurement positions shown in FIG. 2, the matrix contains an entry for the Barkhausen noise signal. In that sense, in relation to the Barkhausen noise signals, the matrix can be regarded as a vector. In a first embodiment of the invention, the matrix M is corrected by means of a correction matrix KM, each correction matrix being specific for one characteristic that represents a cause of grinding burn or some other manufacturing defect of the gearwheel. In what follows, the characteristics of concentricity errors and one-sided grinding will be considered in more detail.

Figure 3:
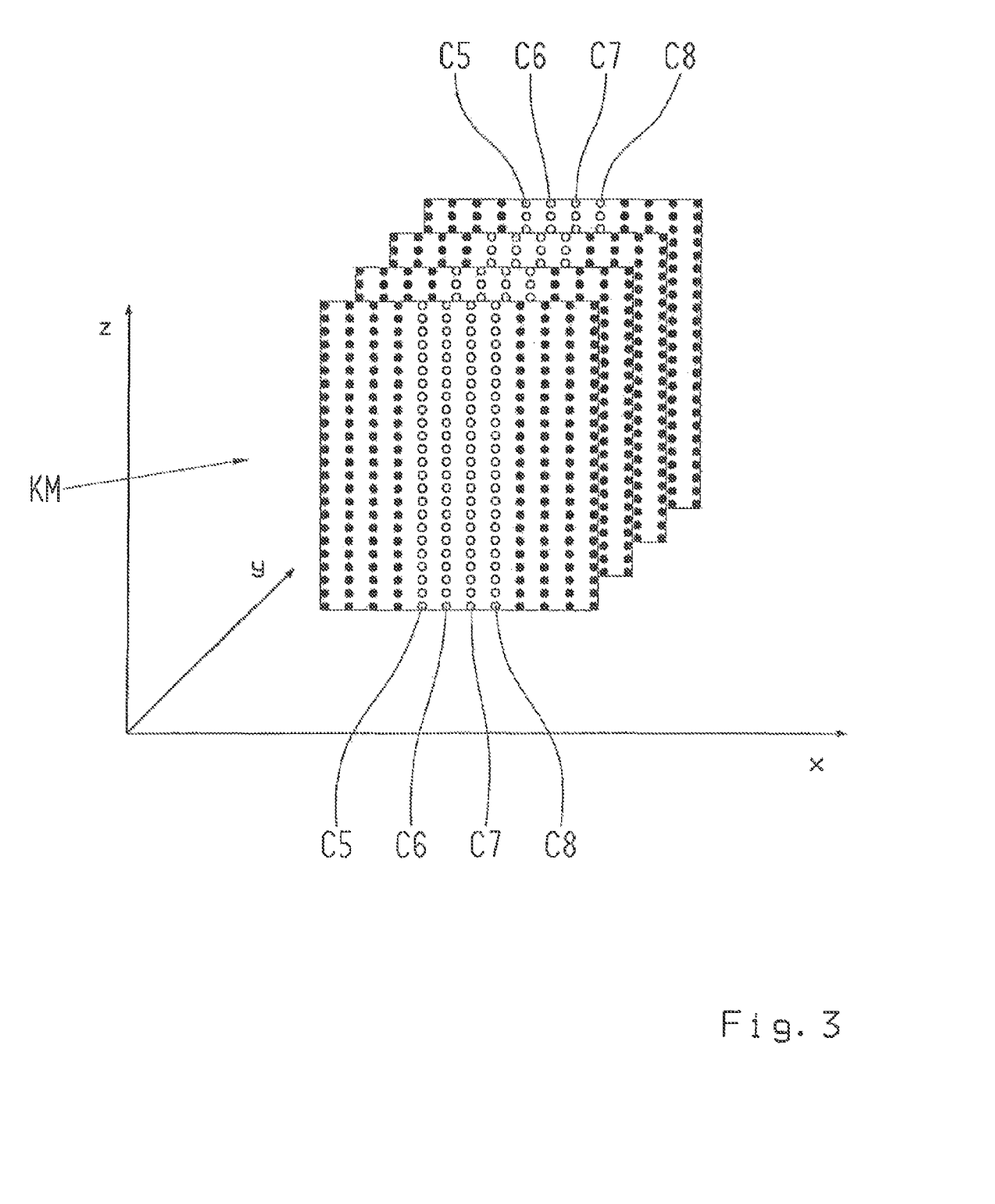
FIG. 3: A graphical representation of a correction matrix for the characteristic of a concentricity error, which is processed in an embodiment of the method according to the invention.

FIG. 3 shows a graphical representation of an embodiment of a correction matrix KM for the characteristic of concentricity error. The matrix in this case contains correction values for each of the measurement positions of the matrix M in FIG. 2. In the version described here the correction values can be 1 and 0. In FIG. 3, a correction value of 1 corresponds to a dark measurement point and a correction value of 0 to a light measurement point. This means that the vertical columns C5, C6, C7 and C8 in each vertical plane of the correction matrix extending parallel to the x-axis have correction values of 1, while in contrast all the other correction values are set at 0. Each correction value is now multiplied by the Barkhausen noise signal in the same position in the measurement matrix of FIG. 2. In this case it should also be borne in mind that the measurement matrix has been pre-processed, since Barkhausen noise signals having the highest signal intensity are arranged centrally relative to the x-axis. In other words, the beginning of the circumferential direction is chosen in such manner that the highest Barkhausen noise signals are located over half the circumference.

The multiplication of the measurement matrix by the correction matrix takes into account that, in the case of concentricity errors, grinding burn and consequently elevated Barkhausen noise signals only occur in a particular circumferential area. Mathematically, the correction matrix KM can be described as follows:

$$KM = \begin{bmatrix} x_1 & y_1 & z_1 & Km_{1,1,1} \\ \dots & \dots & \dots & \dots \\ x_u & y_1 & z_1 & Km_{u,1,1} \\ \dots & \dots & \dots & \dots \\ x_u & y_v & z_1 & Km_{u,v,1} \\ \dots & \dots & \dots & \dots \\ x_u & y_v & z_w & Km_{u,v,w} \end{bmatrix}. \quad (2)$$

in which $Km_{u,v,w}$ is a correction value at the coordinates $[x_u, y_v, z_w]$.

The Barkhausen noise signals of the measurement matrix multiplied by the corresponding entries in the correction matrix are summed, whereby an absolute value of the probability or intensity of the corresponding characteristic is obtained. Thus, the intensity is described mathematically by the following equation:

$$W_i = \sum_u \sum_v \sum_w s_{u,v,w} * Km_{u,v,w}. \quad (3)$$

The summation covers all the tooth flank positions $x_u$, all the measurement line positions $y_v$ and all the tooth width positions $z_w$, so that all the entries in the matrix M are taken into account.

In a preferred embodiment, from the absolute intensity a relative intensity or relative probability of the characteristic is calculated, by dividing $W_i$ by the sum of the intensities of all the characteristics considered. Thus, the relative intensity of a characteristic is described by the following equation:

$$W_{i,rel} = \frac{W_i}{\sum_{i=1}^{n} W_i}. \quad (4)$$

in which n is the number of possible characteristics.

In the case of one-sided grinding in which the tooth flank on the right is ground differently from the tooth flank on the left, the correction values in the matrix KM according to FIG. 3 are distributed differently. In this case the planes of the correction matrix that extend parallel to the y-axis and the z-axis have the correction values 0 and 1 in alternation. In other words, different correction values are assigned to the right-hand and left-hand tooth flanks.

Figure 4:
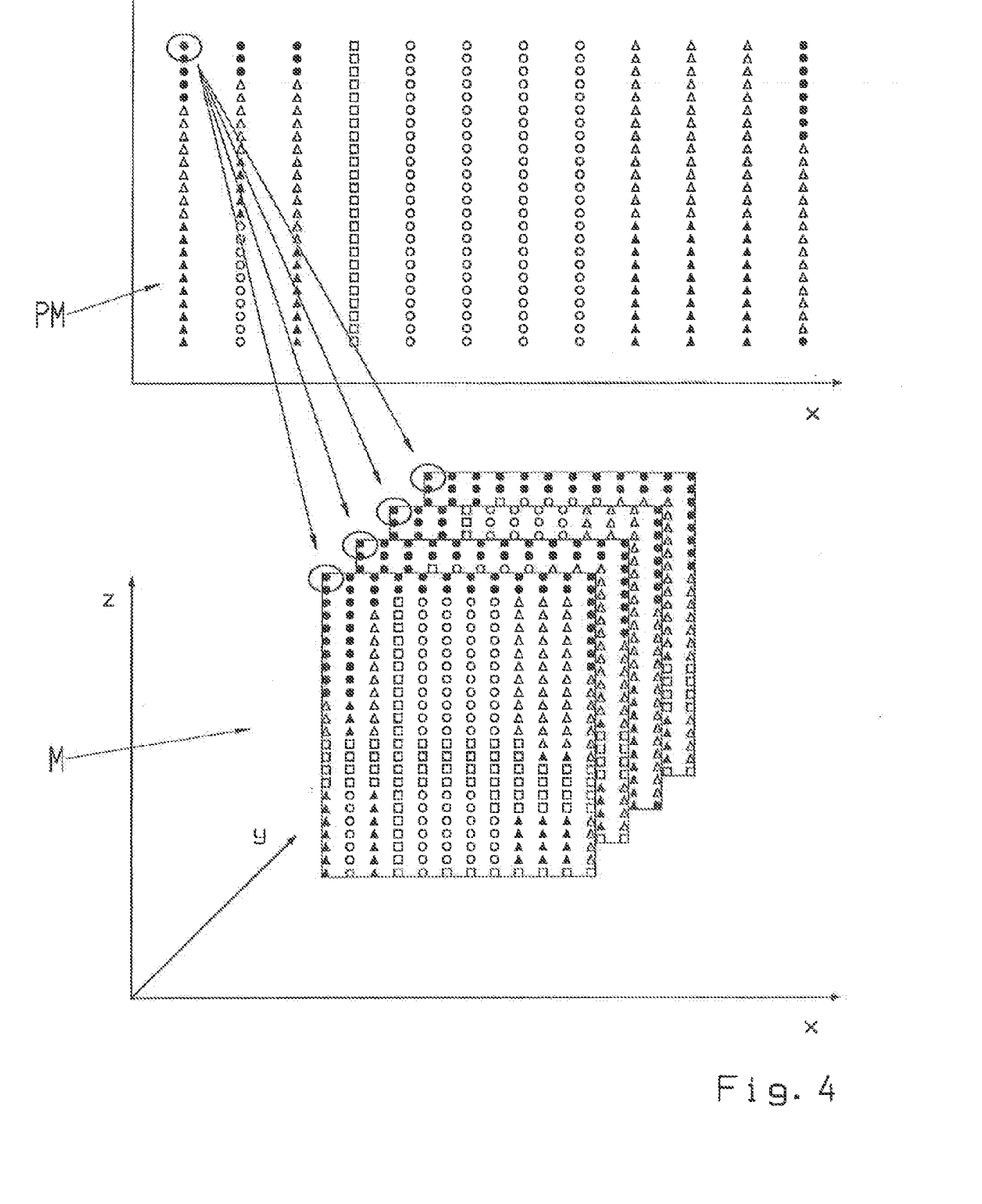
FIG. 4: A schematic representation of a modification of the original measurement matrix, which is carried out in an embodiment of the method according to the invention.

In a further embodiment of the evaluation of the measurement matrix M according to the invention, the corresponding characteristic is described by means of a projection of the measurement matrix that is specific for the characteristic. In this case 'projection' is understood to mean an averaging of the Barkhausen noise signals in the measurement matrix in suitable planes, in accordance with the geometrical description of the gearwheel on the basis of the component's circumference x, the tooth profile y and the width of the tooth z. In the embodiment of FIG. 4, the measurement matrix M is projected in the plane of the x-axis and the z-axis, i.e. the Barkhausen noise signals for equal x-values and z-values, but for different tooth profiles or measurement lines y are averaged. Here, one is making use of the recognition that with such averaging, concentricity errors are again well recognized since the averaging does not take place beyond different circumferential positions of the component. The upper portion of FIG. 4 reproduces the projection matrix PM produced by averaging. In this case, four arrows starting at the top-left entry of the matrix PM indicate which Barkhausen noise signals were included for averaging. It can be seen that these signals relate to the same tooth flanks and the same tooth width, but to different measurement lines.

Mathematically, the projection matrix PM can be described as follows:

$$PM = \begin{bmatrix} \overline{s_{1,0,1}} & \dots & \dots & \overline{s_{1,0,w}} \\ \dots & \dots & \dots & \dots \\ \dots & \dots & \dots & \dots \\ \overline{s_{u,0,1}} & \dots & \dots & \overline{s_{u,0,w}} \end{bmatrix}. \quad (5)$$

in which $\overline{s_{u,0,w}}$ represents the mean value of the Barkhausen noise signals of all the measurement points that have coordinates $x_u$ and $z_w$.

In a suitable manner, projection matrices can also be defined for other characteristics. For example, in the event of one-sided grinding in which, in the direction of the gearwheel's width, more grinding is done on one edge than on the other, care must be taken that the averaging is not carried out over different tooth width positions.

Figure 5:
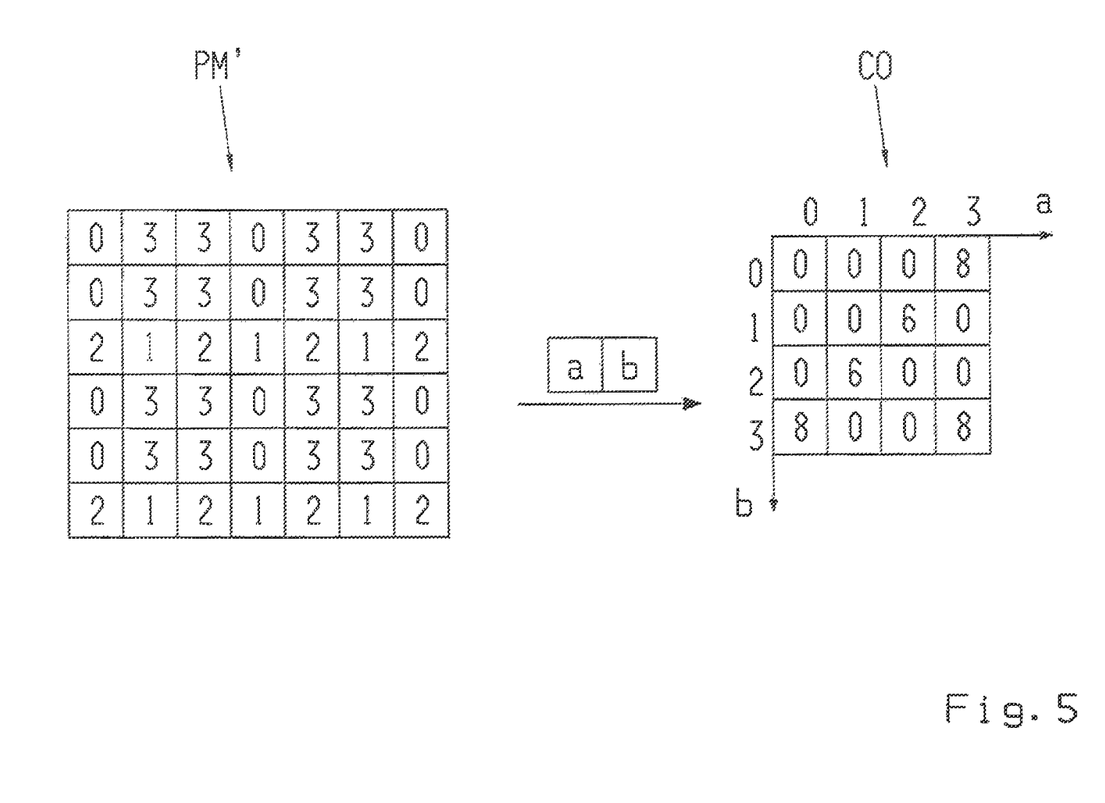
FIG. 5: A schematic representation which makes clear the production of a co-occurrence matrix, which is processed in an embodiment of the method according to the invention.

In a following step, the entries of the PM matrix are now discretized, so that the signals are allocated discrete values in corresponding value ranges. The discretization can be done analogously to the legends in FIG. 2. From this discretized matrix a so-termed co-occurrence matrix is determined, which is known from the field of image processing and is also called a gray scale value matrix. FIG. 5 makes clear the formation of a co-occurrence matrix, considering the example of a discretized matrix PM' that contains four classes 0, 1, 2 and 3 of Barkhausen noise signal intensities, such that a higher class value corresponds to a higher signal intensity. The co-occurrence matrix CO is determined in such manner that for all entries with the corresponding intensity values 0 to 3 plotted in line direction a, it is determined how many immediate neighbors there are with corresponding intensity values 0 to 3 plotted in column direction b. In other words, for every entry of an intensity value it is determined how many immediate neighbors there are with a particular intensity value. Thus, in FIG. 5 the entry at the top right-hand corner of the co-occurrence matrix CO shows the frequency with which an entry with intensity value 3 has an immediate neighbor with an entry having intensity value 0. Accordingly, by means of the co-occurrence matrix marked changes of the intensity of the Barkhausen noise signal can be recognized, these marked changes being represented by large entries in the co-occurrence matrix for elements remote from the diagonal of the matrix.

To evaluate the co-occurrence matrix, in a subsequent step it is multiplied by a weighting matrix GM, which takes into account the fact that a characteristic determined in accordance with the above-described projection is present when there are marked changes of the Barkhausen noise.

Below, an example of a suitable weighting matrix GM for the co-occurrence matrix CO of FIG. 5 is illustrated:

$$GM = \begin{bmatrix} 0 & 1 & 2 & 3 \\ 1 & 0 & 1 & 2 \\ 2 & 1 & 0 & 1 \\ 3 & 2 & 1 & 0 \end{bmatrix}. \quad (6)$$

It can be seen that entries farther away from the diagonal are always more strongly weighted, while in contrast the entries along the diagonal are all equal to 0.

After multiplying the co-occurrence matrix CO by the GM matrix, the final result of an absolute intensity of the characteristic is obtained by forming the determinant of the multiplied matrix, det(CO*GM). The intensity or probability can again be relativized in relation to all the characteristics, by dividing the determinant by the sum of the determinants of all the characteristics. That can be described mathematically as follows:

$$W_i = \frac{\det(CO*GM)}{\sum_i^n \det(CO*GM)}. \quad (8)$$

In the denominator the sum is formed from all possible characteristics. In this case it should be borne in mind that the matrix CO looks different in the denominator for each characteristic, even though in the above formula the same indexes are always used for this matrix.

The embodiments of the invention described above have a series of advantages. In particular, the Barkhausen noise signals detected for a component are evaluated as a function of characteristics which represent causes of grinding burn or process defects. By way of the corresponding intensities these causes can be recognized during the evaluation and thereafter measures can be introduced in order to prevent grinding burn or process defects in the above-mentioned production steps of the component. Thus, not only can components damaged by grinding burn be promptly recognized, but the entire production chain can be optimized.

INDEXES

1 Component
101, 102 Teeth
M1, M2, M3, M4 Measurement lines
h, $b_M/2$, x Height data
PS1, PS2, . . . PS9 Measurement positions
x Tooth flank
y Tooth profile
z Gearwheel width
M Measurement matrix
C5, C6, C7, C8 Columns in the correction matrix
KM Correction matrix
PM Modified measurement matrix
PM' Modified and discretized measurement matrix
CO Co-occurrence matrix
a Lines
b Columns

The invention claimed is:

1. A method of inspecting a component (1) based on Barkhausen noises, in which a plurality of Barkhausen noise signals are processed by a computer unit and which are detected at measurement positions (PS1, PS2, . . . , PS9) along a surface of the component (1) by a measuring device, the method comprising the steps of:
  detecting, with the measuring device, the plurality of the Barkhausen noise signals along the surface of the component;
  forming, with the computer unit, a measurement matrix (M), from the Barkhausen noise signals, which contains the detected Barkhausen noise signals as entries;
  defining a plurality of defect characteristics and correlating each of the plurality of the defect characteristics with at least one cause of a manufacturing defect of the component (1), and associating each of the defect characteristics with a respective specific matrix processing procedure for processing the measurement matrix (M), and the specific matrix processing procedures are specific to the respective defect characteristics associated therewith;
  processing, with the computer unit, the measurement matrix of each of the defect characteristics according to the associated specific matrix processing procedure so as to determine a probability of the defect characteristic associated with the specific processing procedure;
  recognizing, with the computer unit, the causes of the manufacturing defect of the component, and the components having the manufacturing defect based on the probability of the defect characteristic; and
  introducing changes in a component production step that was recognized as the cause of the manufacturing defect of the component so as to prevent the manufacturing defect of the component and to optimize production of further components.

2. The method according to claim 1, wherein the component (1) is a gearwheel, the measurement positions (PS1, PS2, . . . , PS9) at which the Barkhausen noise signals are detected are three-dimensional measurement positions (PS1, PS2, . . . , PS9) at which dimensions of gearwheel circumference (x), tooth profile (y) and gearwheel width (z) are measured with the measuring device, the gearwheel circumference (x) specifies either tooth flanks (101, 102) or tooth gaps along the circumference of the gearwheel, the tooth profile (y) specifies measurement lines (M1, M2, M3, M4) either for a tooth gap or a tooth flank (101, 102), and the gearwheel width (z) specifies width positions in a direction of the width of the gearwheel (1).

3. The method according to claim 1, further comprising the step of defining the defect characteristics and the corresponding cause of the manufacturing defect of the component as being at least one of concentricity errors, one-sided grinding, unmachined positions, dimensional fluctuations, hardening distortions, deviant component surface values and tool wear.

4. The method according to claim 1, further comprising the step of defining a correction matrix which is utilized in the specific matrix processing procedure associated with the respective defect characteristic, the correction matrix (KM) being specific for the defect characteristic concerned, and the correction matrix containing correction values for each of the Barkhausen noise signal entries of the measurement matrix (M), and a sum of the entries of the measurement matrix (M), multiplied by the correction values, is calculated, such that the sum of the entries of the measurement matrix represents an absolute probability of the defect characteristic concerned.

5. The method according to claim 4, wherein the component (1) is a gearwheel, the measurement positions (PS1, PS2, ..., PS9) at which the Barkhausen noise signals are detected are three-dimensional measurement positions (PS1, PS2, ..., PS9) at which dimensions of gearwheel circumference (x), tooth profile (y) and gearwheel width (z) are measured with the measuring device, the gearwheel circumference (x) specifies either tooth flanks (101, 102) or tooth gaps along the circumference of the gearwheel, the tooth profile (y) specifies measurement lines (M1, M2, M3, M4) either for a tooth gap or a tooth flank (101, 102), and the gearwheel width (z) specifies width positions in a direction of the width of the gearwheel (1);

further comprising the step of defining the defect characteristics and the corresponding cause of the manufacturing defect of the component as being at least one of concentricity errors, one-sided grinding, unmachined positions, dimensional fluctuations, hardening distortions, deviant component surface values and tool wear; and for the defect characteristic of concentricity error, the correction values for all of the Barkhausen noise signals measured at the measurement positions (PS1, PS2, ..., PS9) within a predetermined circumferential region are set to either one or zero, and for the defect characteristic of one-sided grinding, the correction values alternate between zero and one from one tooth flank to a next tooth flank, and within the tooth flank, the correction values either remain the same or the correction value at an edge area of the gearwheel's width is set at one or zero.

6. The method according to claim 1, wherein the matrix processing procedure associated with each of respective defect characteristic comprises a modification step in which a modified measurement matrix (PM) is determined by averaging the Barkhausen noise signals from a number of the measurement positions (PS1, PS2, ..., PS9) along the surface of the component (1), and the number of the measurement positions (PS1, PS2, ..., PS9) are specific for each of the respective defect characteristics.

7. The method according to claim 6, wherein the component (1) is a gearwheel, the measurement positions (PS1, PS2, ..., PS9) at which the Barkhausen noise signals are detected are three-dimensional measurement positions (PS1, PS2, ..., PS9) at which dimensions of gearwheel circumference (x), tooth profile (y) and gearwheel width (z) are measured, the gearwheel circumference (x) defines either tooth flanks (101, 102) or tooth gaps along the circumference of the gearwheel, the tooth profile (y) defines measurement lines (M1, M2, M3, M4) either for a tooth gap or a tooth flank (101, 102), and the gearwheel width (z) defines width positions in direction of the width of the gearwheel (1);

further comprising the step of defining the defect characteristics and the corresponding cause of the manufacturing defect of the component as being at least one of concentricity errors, one-sided grinding, unmachined positions, dimensional fluctuations, hardening distortions, deviant component surface values and tool wear; and for the defect characteristic of concentricity error, the measurement positions (PS1, PS2, ..., PS9) whose Barkhausen noise signals are averaged, are exclusively measurement positions (PS1, PS2, ..., PS9) that relate to the same tooth flank (101, 102) or the same tooth gap, and for the defect characteristic of one-sided grinding, the measurement positions (PS1, PS2, ..., PS9) whose Barkhausen noise signals are averaged, are exclusively measurement positions (PS1, PS2, ..., PS9) relating either to the same tooth flank (101, 102) or the same width position of the gearwheel width (z).

8. The method according to claim 6, wherein, besides the modification step, the matrix processing procedure associated with each of the defect characteristics comprises a processing step in which entries of the modified measurement matrix (PM) are discretized and a co-occurrence matrix (CO) is determined for frequencies of value combinations of neighboring entries in a modified and discretized measurement matrix (PM'), the co-occurrence matrix (CO) is then multiplied by a weighting matrix which assigns greater weight to large changes in the values of neighboring entries in the modified and the discretized measurement matrix (PM'), and calculating a determinant of the multiplication result, this determinant representing an absolute probability of the respective defect characteristic concerned.

9. The method according to claim 1 further comprising the steps of defining a correction matrix which is utilized in the specific matrix processing procedure associated with the respective defect characteristic, the correction matrix (KM) being specific for the defect characteristic concerned, the correction matrix containing correction values for each of the Barkhausen noise signal entries forming the measurement matrix (M), and a sum of the entries of the measurement matrix (M) multiplied by the correction values is calculated, such that the sum of the entries of the measure matrix represents an absolute probability of the defect characteristic concerned; and determining, with the computer unit, a relative probability from the absolute probability of any of the defect characteristics by dividing the absolute probability of the defect characteristic by a sum of the absolute probabilities of all the defect characteristics.

10. A device for inspecting a component (1) based on Barkhausen noises using a plurality of Barkhausen noise signals that are determined at measurement positions (PS1, PS2, ..., PS9) along a surface of the component (1) by a measuring device, wherein the device for inspecting the component comprises a computer unit which, during operation, forms a measurement matrix (M), from the plurality of the Barkhausen noise signals, the measurement matrix contains the Barkhausen noise signals as entries;

a plurality of defect characteristics are defined such that each of the defect characteristics correlates with at least one cause of manufacturing defects of the component (1), and each of the plurality of defect characteristics is associated with a matrix processing procedure for processing the measurement matrix (M), and the matrix processing procedure being specific for the defect characteristic concerned; and for each of the defect characteristics, the measurement matrix (M) undergoes the associated matrix processing procedure to determine a probability of the defect characteristic.

11. The device according to claim 10, wherein the device facilitates a method for inspecting the component comprising the steps of:

detecting, with the measuring device, the plurality of Barkhausen noise signals at the measurement positions along the surface of the component;

forming, with the computer unit, from the Barkhausen noise signals, the measurement matrix (M) which contains the detected Barkhausen noise signals as the entries;

defining the plurality of defect characteristics such that each of the plurality of the defect characteristics represents at least one of the causes of the manufacturing defects of the component (1), and correlating each of the defect characteristics with a matrix processing procedure of the measurement matrix (M), the matrix processing procedures are specific to the respective defect characteristics associated therewith; and processing, with the computer unit, the measurement matrix of each of the defect characteristics according to the associated matrix processing procedure so as to determine the probability of the defect characteristic associated with the matrix processing procedure;

recognizing, with the computer unit, the causes of the manufacturing defect of the component and the components having the manufacturing defect based on the probability of the defect characteristic; and adjusting at least one component production step that is recognized as the cause of the manufacturing defect of the component to prevent the manufacturing defect of the component and to optimize production of further components.

12. A method of inspecting a gearwheel (1) for at least one manufacturing defect, each of the manufacturing defects being caused by at least one manufacturing step and corresponds to an associated specific gearwheel defect characteristic, the method comprising the steps of:

determining, with a measuring device, a plurality of Barkhausen noise signals from a plurality of measurement positions along a surface of the gearwheel;

forming, with a computer, a measurement matrix for the specific gearwheel defect characteristic;

processing the measurement matrix for each of the specific gearwheel defect characteristics to determine a probability of the respective specific gearwheel defect characteristics;

recognizing the causes of the at least one manufacturing defect based on the determined probability of each of the specific gearwheel defect characteristics; and adjusting the at least one manufacturing step that was recognized as being the cause of the manufacturing defect to prevent the manufacturing defect and optimize manufacture of further gearwheels.

* * * * *